United States Patent [19]

Ask et al.

[11] Patent Number: 5,227,389
[45] Date of Patent: Jul. 13, 1993

[54] SUBSTITUTED 4-PHENYL-4-PIPERIDINECARBOXAMIDES WITH BOTH LOCAL ANAESTHETIC AND ANALGESIC EFFECT AS WELL AS PROCESSES FOR THEIR PREPARATION

[75] Inventors: Anna-Lena Ask, Huddinge; Rune V. Sandberg, Järna, both of Sweden

[73] Assignee: Aktiebolaget Astra, Sodertalje, Sweden

[21] Appl. No.: 633,246

[22] Filed: Dec. 21, 1990

[30] Foreign Application Priority Data

Dec. 21, 1989 [SE] Sweden .................. 8904298

[51] Int. Cl.$^5$ .................. A61K 31/445; C07D 211/30
[52] U.S. Cl. .................. 514/330; 546/189; 546/208; 546/225
[58] Field of Search .................. 546/225, 194, 189; 514/330

[56] References Cited

U.S. PATENT DOCUMENTS 2,486,796 12/1946 Miescher .................. 546/225

FOREIGN PATENT DOCUMENTS 2156470 6/1973 France .
0501622 12/1968 Switzerland .

OTHER PUBLICATIONS

Chodkowski, et al. Acta. Polon. Pharm. 36, 439-442 (1979).
Janicki, et al. Chemical Abstracts 95:35457t (1981).
Lasslo, et al., Journal of Medicinal and Pharmaceutical Chemistry, 2, 107-110 (1960).
Longo, et al., Proceedings of the International Pharmacology Meeting, vol. 8, 189-198 (1961).
Chodkowski, et al. CA 93:7971(w): 1979.

*Primary Examiner*—Glennon H. Hollrah
*Assistant Examiner*—B. M. Burn
*Attorney, Agent, or Firm*—White & Case

[57] ABSTRACT

Compounds of the formula IV for use as local anesthesia and analgesia, as well as a method for their preparation, their pharmaceutical preparations and their use.

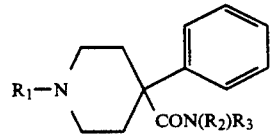

IV

7 Claims, No Drawings

SUBSTITUTED 4-PHENYL-4-PIPERIDINECARBOXAMIDES WITH BOTH LOCAL ANAESTHETIC AND ANALGESIC EFFECT AS WELL AS PROCESSES FOR THEIR PREPARATION

FIELD OF THE INVENTION

The present invention is directed to new compounds having both local anaesthetic and analgesic effect, a process for their preparation and their use in the manufacture of pharmaceutical preparations.

BACKGROUND OF THE INVENTION

Pethidine is a frequently used analgesic. It has also a weak local anaesthetic effect. The anaesthetic/analgesic effect of pethidine after spinal administration is often insufficient in both respects. Instead combinations of bupivacaine and fentanyl or morfin are being used. The opiate analgesics have several severe draw-backs, as e.g. development of tolerance, addiction, risk for respiratory depression. There is, thus, a need for agents giving a local anaesthesia with a remaining analgesic effect. Such agents should be used after spinal or epidural injections as local anaesthetics intraoperatively. Thereafter the compounds would give good post-operative pain relief.

PRIOR ART

Hardy D. G. et al describe in J. Med. Chem. 8, pp. 847-851 (1965) the structure-activity relationship of some analogues of pethidine, which have an analgesic activity. The Swedish patent 96980 describes 1-methyl-4-phenylpiperidin-4-carboxylic acid and two amides thereof. No specific pharmaceutical effect is given in the document, only that the compounds can be used in the manufacture of new drugs. From FR 2156470 derivatives of 1-(3,3-diphenylpropyl)-piperidine are know, which due to their high lipid solubility only can be active as analgetics not as local anaesthetics. In Acta Pol Pharm 1979,36(4), p. 439-4, (Chemical Abstracts 93(1980) 7970v) some amides of 1-butyl-4-phenyl-4-piperidinecarboxylic acid are described. These amides seem to have analgesic, but not local anaesthetic effect.

Outline of the Invention

It has been found that compounds of the following formula IV or pharmaceutically acceptable salts thereof not only give an unexpectedly good effect as spinal and epidural anaesthetics but also have an additional analgesic effect that lasts for a long time after the anaesthetic effect has declined. Thus no combination of active compounds need to be given, thus avoiding the risks connected with these mentioned above. The compounds according to the invention are defined by the following formula IV

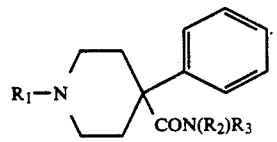

wherein
$R_1$ is an alkyl group with 2-6 carbon atoms or an alkoxyalkyl group $R_4O-(CH_2)_m-$, wherein $R_4$ is an alkyl group with 1-4 carbon atoms and m is 2-4, $R_2$ and $R_3$ are the same or different and each an alkyl group with up to 6 carbon atoms or $R_2$ and $R_3$ form together a chain $(CH_2)_n$ wherein n is 4-6 or one of $R_2$ and $R_3$ is hydrogen and a straight or branched alkyl group with 1-6 carbon atoms as well as pharmaceutically acceptable salts thereof.

Preferred compounds according to the invention are those, wherein $R_1$, $R_2$ and $R_3$ are alkyl groups.

Especially preferred is the compound wherein the group $R_1$ is hexyl, $R_2$ is methyl or ethyl and $R_3$ is ethyl.

Preferred salts according to the invention are pharmaceutically acceptable salts. The hydrochloride is especially preferred.

Preparation

Compounds of the formula IV above were prepared according to the following:

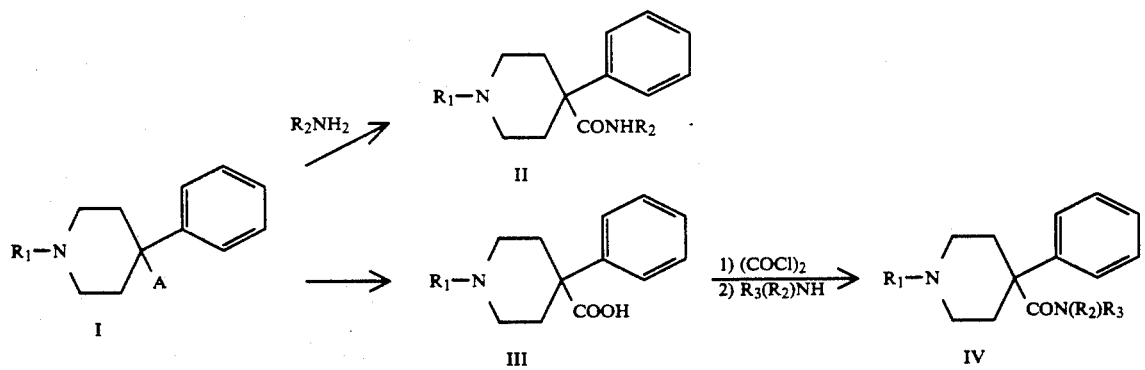

wherein A, $R_1$, $R_2$, and $R_3$ are as defined above.

The compounds of the formula I wherein A is CN or $-CO_2C_2H_5$ and $R_1$ is as defined above were prepared from the corresponding secondary amine ($R_1=H$) with the exception of the compound wherein $R_1$ is $CH_3$ and A is $CO_2C_2H_5$, which is the commercially available compound pethidine. The compounds of the formula II are prepared directly form I wherein A is $-CO_2C_2H_5$ (c.f. Example 1) by reaction with an alkylamine or are prepared in the same way as the compounds of the formula IV. These are obtained by first hydrolyzing the compounds of the formula I to the carboxylic acids of the formula III, which then are reacted with oxalyl chloride and the appropriate amine to yield a compound of the formula IV.

Detailed Description of the Preparation

The examples denoted I1–I6 describe intermediates in the preparation of the compounds of the formula IV.

COMPOUNDS I

Example I 1

Ethyl 1-hexyl-4-phenyl-4-piperidine carboxylate hydrochloride

Norpethidine (23.5 g, 0.10 mol), hexyliodide (23.5 g, 0.11 mol), anhydrous $Na_2CO_3$ (11.7 g, 0.11 mol) and acetonitrile (250 ml) were heated under reflux and stirring for 1,5 h. The mixture was filtered and the solvent removed. The residue was dissolved in $CH_2Cl_2$, the solution washed with 100 ml of 1 N NaOH and then with water and finally dried ($K_2CO_3$). To the solution HCl (g) in diethyl ether was then added, whereupon the solvents were removed and the residue recrystallized from ethyl acetate. Yield 22.5 g of hydrochloride with m.p. 156°–158° C.

M.p. acc. to J. Med.Chem. 8 p. 847–851 (1965), 158° C.

Example I 2

Ethyl 1-[4-ethoxybutyl]-4-phenyl-4-piperidinecarboxylate hydrochloride

Norpethidine (15.63 g, 67 mmol), 4-ethoxybutylchloride (10.67 g, 70 mmol), $Na_2CO_3$ (7.77 g, 73 mmol), KI (0.6 g) and acetonitrile (150 ml) were heated under reflux and stirring for 72 h. The mixture was filtered and the solvent removed. The residue was dissolved in diethyl ether, and the solution washed with water and dried ($MgSO_4$). Destillation yielded 17.9 g of base boiling at 160°–163° C./0.05 mm Hg. B.p. acc. to J. Chem. Soc. 3062 (1958) 180° C./1 mm Hg. Hydrochloride m.p. 143°–145° C.

Example I 3

1-(2-Ethoxyethyl)-4-cyano-4-phenyl-piperidine

The title compound was prepared as described in Example I 2 from 4-cyano-4-phenylpiperidine and 2-bromoethyl ethyl ether excluding KI: Reaction time under reflux 6 hours. The compound boiled at 130°–135°/0.005 mm Hg.

COMPOUNDS III

Example I 4

1-Hexyl-4-phenyl-4-piperidinecarboxylic acid hydrochloride

A mixture of the ethyl ester (22.5 g, 64 mmol) 20% hydrochloric acid (225 ml) and acetic acid (70 ml) was heated under reflux for 30 h. After cooling the mixture was poured into 200 ml of ice water, the acid was filtered and air dried. Yield 12.9 g. The filtrate was evaporated and the residue treated with acetonitrile yielding another 4 g of acid. Recrystallization from acetonitril yielded 16.9 g with m.p. 193°–195° C. The acid contains solvent of crystallization.

EXAMPLE I 5

1-[4-Ethoxybutyl]-4-phenyl-4-piperidinecarboxylic acid hydrochloride

A mixture of the ethyl ester (17.9 g, 53.7 mmol), 2N NaOH (55 ml) and ethanol (6 ml) was heated under reflux with stirring for 24 h. The solution was extracted with diethyl ether and then acidified with dilute hydrochloric acid. The solvent was evaporated and the residue extracted with acetone. The acetone solution was filtered and the solvent evaporated. The crystalline residue was dried over $CaCl_2$ in a vacuum desiccator and the recrystallized from THF-ethyl acetate. Yield 11.7 g with m.p. 131°–133° C.

Example I 6

1-(2-Ethoxyethyl)-4-phenyl-4-piperidine-carboxylic acid hydrochloride

A mixture of the cyanide according to example I 3 (5.6 g), KOH(5.6 g), ethanol (39 ml) and water (17 ml) was heated in an autoclave at 140° C. for 6 hours. The reaction mixture was acidified with concentrated hydrochloric acid, the precipitated salt was filtered and the filtrate evaporated. The residue was leached with hot acetone. From the acetone extracts 4.2 g of the title compound was obtained. m.p. 150°–155° C.

COMPOUNDS II

Example 1

N-Butyl-1-methyl-4-phenyl-4-piperidinecarboxamide

Pethidine hydrochloride (2.56 g, 9 mmol) and butylamine (5 ml) were heated in an autoclave at 180° C. for 3 days. The reaction mixture was shaken between 10 ml of 1N NaOH and diethyl ether and the ether extracts dried ($MgSO_4$). The solvent was evaporated and the residue chromatographed on aluminium oxide with ethyl acetate as eluent. The crystalline product (1.0 g) was recrystallized from n-hexane yielding 0.59 g with m.p. 73°–76.5° C.

Example 3

N-Ethyl-1-hexyl-4-phenyl-4-piperidinecarboxamide

This compound was prepared as above form ethyl 1-hexyl-4-phenyl-4-piperidinecarboxylate hydrochloride (3.54 g, 10 mmol) and ethylamine (2.25 g, 50 mmol). Reaction time 2 days. The crude product (1.0 g) was recrystallized from disopropyl ether, yielding 0.81 g with m.p. 92°–94° C. Hydrochloride m.p. 221°–223° C. (form 2% aqueous acetone).

COMPOUNDS IV

General method of preparation. Oxalyl chloride (4 ml) was added dropwise with stirring to a solution of a piperidinecarboxylic acid (compounds III) (5–6 mmol) in $CH_2Cl_2$ (20 ml). The reaction mixture was stirred at 50° C. for 2 h. The solvent was evaporated, a few ml of toluene were added and the solvent was evaporated again. The residue was dissolved in $CH_2Cl_2$ (10 ml) and the solution was added dropwise with stirring to a solution of the appropriate amine (35–42 mmole) in $CH_2Cl_2$ (20 ml), cooled in ice-water. The reaction mixture was then stirred at room temperature for a few hours. It was then shaken with 1N NaOH (20 ml), once with water, dried ($K_2CO_3$) and the solvent evaporated.

Before conversion to hydrochloride the crude base in several cases was further purified e.g. by chromatography.

In the following Table 1 some compounds according to the invention are given.

TABLE 1

R₁—N⟨piperidine⟩(C₆H₅)CON(R₂)R₃

| Comp | R₁ | R₂ | R₃ | hydrochloride m.p °C. |
|---|---|---|---|---|
| 1) | CH₃ | H | C₄H₉ | 73–76.5 |
| 2) | C₆H₁₃ | H | CH₃ | 252–254 |
| 3) | C₆H₁₃ | H | C₂H₅ | 221–223 |
| 4) | C₆H₁₃ | H | CH(CH₃)₂ | 145–148 |
| 5) | C₆H₁₃ | CH₃ | CH₃ | 155.5–158.5 |
| 6) | C₆H₁₃ | CH₃ | C₂H₅ | 137–141 |
| 7) | C₆H₁₃ | C₂H₅ | C₂H₅ | 151–154 |
| 8) | C₆H₁₃ | (CH₂)₅ | | 217–219 |
| 9) | C₂H₅O(CH₂)₄ | CH₃ | CH₃ | 125–128 |
| 10) | C₂H₅O(CH₂)₄ | CH₃ | C₂H₅ | 115–117 |
| 11) | C₂H₅O(CH₂)₄ | (CH₂)₅ | | 130–132 |
| 12) | C₂H₅OCH₂—CH₂ | C₂H₅ | C₂H₅ | 142–144 |
| 13) | C₃H₇O(CH₂)₂ | C₂H₅ | C₂H₅ | |
| 14) | C₄H₉O(CH₂)₂ | C₂H₅ | C₂H₅ | |

Pharmaceutical preparations

For the preparation of pharmaceutical preparations the new compound is dissolved in a liquid diluent which is suitable for injection. The preparations used are aqueous solutions which contain between 2.5 and 40.0 mg/ml of the active compound calculated as the hydrochloride salt.

Biological studies

Spinal anaesthesia

The compounds according to the invention were tested for spinal anaesthesia in the mouse. There were six animals in each group. As reference compound pethidine, the starting materials for compounds 2) - 8), namely ethyl 1-hexyl-4-phenyl-4-piperidinecarboxylate hydrochloride (Example I 1) and 9) and 10), namely ethyl 1-[4-ethoxybutyl]-4-phenyl-4-piperidinecarboxylate hydrochloride, (Example I 2) known from the above cited J. Med. Chem. were tested. The results are presented int he following Table 2.

TABLE 2

Mean duration (min) of motor block and full analgesia (tail-flick) in mice after subarachnoid injection of 5 µl of the test solution. The durations are calculated from the time of injection.

| Compound | Conc. % | Motor bl Duration | Tail-flick min |
|---|---|---|---|
| 3 | 1 | 10 | 15 |
| 4 | | 14 | 35 |
| 5 | | 14 | 20 |
| 6 | | 20 | 40 |
| 7 | | 27 | 50 |
| 8 | | 19 | 40 |
| 9 | | 3 | 10 |
| 10 | | 6 | 10 |
| 11 | | 6 | 10 |
| 12 | | 3 | 10 |
| I 1 | | 15 | 40 |
| I 2 | | 5 | 25 |
| 3 | 2 | 22 | 30 |
| 4 | | 24 | 30 |
| 5 | | 21 | 25 |
| 6 | | 36 | 55 |
| 7 | | 48 | 85 |
| 8[1] | | 49 | >120 |
| 9 | | 6 | 10 |
| 10 | | 7 | 10 |
| 11 | | 12 | 35 |
| 12 | | 6 | 10 |
| I 2 | | 10 | 15 |
| Pethidine | | 4 | 15 |
| 1 | 4 | 17 | 20 |
| Pethidine | | 10 | 25 |

[1]The animals were irritated, squeaky

Discussion

As can be seen from Table 2 the compounds according to the invention give a better local anaesthetic effect than the known analgesic pethidine. As the local anaesthetic effect is combined with a good analgesic effect, the compounds according to the invention are more useful than pethidine. They can also replace the combinations of one analgesic and one anaesthetic agent with good result.

The best mode of carrying out the invention known at present is to sue the compounds 6 or 7.

We claim:

1. Compounds of the formula IV

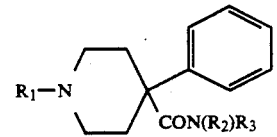

wherein R₁ is hexyl R₂ and R₃ are the same or different and each an alkyl group with up to 6 carbon atoms or one of R₂ and R₃ is hydrogen and the other is a straight or branched alkyl group with 1–6 carbon atoms as well as pharmaceutically acceptable salts thereof.

2. A compound according to claim 1, wherein R₁, R₂ and R₃ are alkyl groups.

3. A compound according to claim 2, wherein R₂ is methyl and R₃ is ethyl.

4. A compound according to claim 2, wherein R₂ and R₃ are both ethyl.

5. A pharmaceutical preparation containing a compound according to claim 1 in a liquid diluent for local anaesthetic block of the epidural or intrathecal route.

6. A pharmaceutical preparation containing a compound according to claim 1 in a liquid diluent for anaesthesia and analgesia.

7. A method for inducing anaesthesia and analgesia comprising the administration to mammals including man needing local anaesthesia and analgesia of an effective amount of a compound according to claim 1 in a liquid diluent.